(12) United States Patent
Feldman et al.

(10) Patent No.: US 10,420,952 B2
(45) Date of Patent: Sep. 24, 2019

(54) METHOD AND APPARATUS FOR TREATING A PATIENT'S HEART USING HEMODYNAMICS

(71) Applicants: Marc D. Feldman, San Antonio, TX (US); Erik R. Larson, Austin, TX (US); John A. Pearce, Austin, TX (US); Jonathan W. Valvano, Austin, TX (US); John Porterfield, Austin, TX (US)

(72) Inventors: Marc D. Feldman, San Antonio, TX (US); Erik R. Larson, Austin, TX (US); John A. Pearce, Austin, TX (US); Jonathan W. Valvano, Austin, TX (US); John Porterfield, Austin, TX (US)

(73) Assignees: Board of Regents, The University of Texas System, Austin, TX (US); Admittance Technologies, Inc., San Antonio, TX (US)

( * ) Notice: Subject to any disclaimer, the term of this patent is extended or adjusted under 35 U.S.C. 154(b) by 0 days.

(21) Appl. No.: 13/648,725

(22) Filed: Oct. 10, 2012

(65) Prior Publication Data

US 2014/0100621 A1    Apr. 10, 2014

(51) Int. Cl.
*A61N 1/39* (2006.01)
*A61B 5/02* (2006.01)
*A61B 5/00* (2006.01)

(52) U.S. Cl.
CPC ............ *A61N 1/39* (2013.01); *A61B 5/02028* (2013.01); *A61B 5/4836* (2013.01); *A61B 5/686* (2013.01)

(58) Field of Classification Search
CPC .............. A61N 1/36521; A61N 1/3962; A61N 1/3627; A61N 1/3702; A61N 1/3925; A61B 5/053; A61B 5/02028
USPC ......................... 607/4, 17, 23; 600/486, 508
See application file for complete search history.

(56) References Cited

U.S. PATENT DOCUMENTS

| | | | |
|---|---|---|---|
| 5,197,467 A * | 3/1993 | Steinhaus | A61N 1/36521 600/547 |
| 6,112,115 A | 8/2000 | Feldman et al. | |
| 6,494,832 B1 | 12/2002 | Feldman et al. | |
| 7,925,335 B2 | 4/2011 | Feldman et al. | |
| 7,970,465 B1 * | 6/2011 | Kroll | A61N 1/3962 607/18 |
| 8,706,219 B2 | 4/2014 | Feldman et al. | |
| 2008/0200961 A1 * | 8/2008 | Kroll et al. | 607/17 |
| 2009/0210020 A1 | 8/2009 | Feldman et al. | |
| 2010/0174206 A1 * | 7/2010 | Kamousi | A61B 5/0464 600/518 |
| 2010/0217342 A1 * | 8/2010 | Hamdan | A61N 1/3962 607/4 |

(Continued)

*Primary Examiner* — Nicole F Lavert
(74) *Attorney, Agent, or Firm* — Ansel M. Schwartz

(57) ABSTRACT

An apparatus for treating a patient's heart includes a sensor for measuring hemodynamics of the heart. The apparatus includes a processing unit which receives the hemodynamics from the sensor and uses the hemodynamics to determine whether to shock the heart. A method for treating a patient's heart. The method includes the steps of measuring hemodynamics of the heart with a sensor. There is the step of receiving the hemodynamics from the sensor at a processing unit which uses the hemodynamics to determine whether to shock the heart.

9 Claims, 9 Drawing Sheets

(56) References Cited

U.S. PATENT DOCUMENTS

| | | | |
|---|---|---|---|
| 2010/0280397 A1* | 11/2010 | Feldman | A61N 1/3962 600/486 |
| 2011/0152661 A1 | 6/2011 | Feldman et al. | |
| 2011/0224748 A1* | 9/2011 | Lippert | A61B 5/02028 607/7 |
| 2011/0282405 A1* | 11/2011 | Hauck | A61B 5/0464 607/5 |
| 2012/0150252 A1* | 6/2012 | Feldman et al. | 607/18 |
| 2013/0023946 A1 | 1/2013 | Valvano et al. | |

* cited by examiner

METHOD AND APPARATUS FOR TREATING A PATIENT'S HEART USING HEMODYNAMICS

CROSS-REFERENCE TO RELATED APPLICATIONS

This is a nonprovisional of U.S. provisional patent application Ser. No. 61/627,900 filed Oct. 20, 2011, and is a continuation-in-part of U.S. patent application Ser. No. 13/425,119, and publication number 20130023946, filed Mar. 20, 2012, which is a nonprovisional of U.S. provisional application Ser. No. 61/516,138 filed Mar. 20, 2011, and is a continuation-in-part of U.S. patent application Ser. No. 13/373,850, and publication number 20120150252, filed Dec. 2, 2011, which is a nonprovisional of U.S. provisional patent application Ser. No. 61/459,280 filed Dec. 10, 2010, all of which are incorporated by reference herein.

FIELD OF THE INVENTION

The present invention is related to treating a patient's heart by using the hemodynamics of the heart to determine whether to shock the heart.

BACKGROUND OF THE INVENTION

This section is intended to introduce the reader to various aspects of the art that may be related to various aspects of the present invention. The following discussion is intended to provide information to facilitate a better understanding of the present invention. Accordingly, it should be understood that statements in the following discussion are to be read in this light, and not as admissions of prior art.

Implantable Cardioverter Defibrillators (ICDs) are implantable medical devices (IMDs) proven to prevent sudden cardiac death (SCD) due to ventricular arrhythmia and thus prolong life. ICDs perform therapy by sensing arrhythmia, and delivering timed anti-tachycardial pacing (ATP) or in cases where this does not work, they defibrillate the heart by delivering a shock to convert the heart to normal sinus rhythm.

ICDs have at least one lead implanted in a chamber of the heart, and up to 3 leads for CRT+ICD devices. The majority of these devices rely on accurate classification of the electrical signals (intracardiac ECGs) that are sensed on one or more electrodes implanted in various chambers of the heart. If an electrical arrhythmia is detected, the ICD determines whether to shock or to pace the heart to convert the rhythm back to normal sinus rhythm before hemodynamic instability occurs. Alternatively, sinus tachycardia can occur which would be neither paced nor shocked, but observed. These determinations are currently made without knowledge of the hemodynamic status of the heart, which can cause the device to misclassify some arrhythmias that do not need treatment causing an "inappropriate shock". In contrast, when physicians treat patients having ongoing arrhythmias with congestive heart failure from dilated and failing left ventricles, they are trained to determine hemodynamic parameters such as blood pressure or cardiac output (stroke volume). If the blood pressure and cardiac output (stroke volume) are adequate, they are trained to attempt conservative measures to terminate the arrthymia such as pacing or iv administration of medications. However, if the blood pressure or cardiac output (stroke volume) are unstable and too low, then physicians are trained to administer cardioversion (electrical shocks).

It has been reported that anywhere from 20-35% of patients who receive an ICD will experience an "appropriate" shock within the first 1-3 years of receiving the implant. Around a third of patients who receive an ICD experience an "inappropriate" shock, indicating that therapy was delivered unnecessarily, and the remaining third do not receive a shock (2). Receiving shock therapy is associated with a two- to five-fold increase in mortality in these patients, so the elimination of unnecessary shocks has become an important focus in ICD research within the last decade. The main reasons for a device delivering an inappropriate shock are:

1. An atrial fibrillation (AF) or other supra-ventricular tachycardia (SVT) event including sinus tachycardia which is misclassified as a more serious rhythm such as ventricular tachycardia or fibrillation.
2. The ICD misclassifies the rate of the heart because it counts the heart rate twice for every beat (called oversensing) by misreading the QRS complex and T wave.
3. Mechanical problems such as lead fracture, or dislodgement of the lead.

The first two of these problems occur because the electrical system of the heart (ECG) is being used to determine cardiac hemodynamics. Clearly, a more direct measurement of hemodynamics would be more useful.

Background Bibliography, all of which is Incorporated by Reference

1. Daubert J C, Leclercq C, Mabo P. Cardiac resynchronization therapy in combination with implantable cardioverter-defibrillator. Europace. 2009; 11 Suppl 5:v 87-92.
2. Mishkin J D, Saxonhouse S J, Woo G W, Burkart T A, Miles W M, Conti J B, et al. Appropriate evaluation and treatment of heart failure patients after implantable cardioverter-defibrillator discharge: time to go beyond the initial shock. J Am Coil Cardiol. 2009; 54(22):1993-2000.
3. Wilkoff B L, Williamson B D, Stem R S, Moore S L, Lu F, Lee S W, et al. Strategic programming of detection and therapy parameters in implantable cardioverter-defibrillators reduces shocks in primary prevention patients: results from the PREPARE (Primary Prevention Parameters Evaluation) study. J Am Coll Cardiol. 2008; 52(7):541-50.
4. Poole J E, Johnson G W, Helikamp A S, Anderson J, Caftans D J, Raitt M H, et al. Prognostic importance of defibrillator shocks in patients with heart failure. N Engl J Med. 2008; 359(10):1009-17.
5. Francia P, Balla C, Uccellini A, Cappato R. Arrhythmia detection in single- and dual-chamber implantable cardioverter defibrillators: the more leads, the better? J Cardiovasc Electrophysiol. 2009; 20(9):1077-82.

Prior Art, all of which is Incorporated by Reference a) Czygan G, Lippert M, inventors; Biotronik GmbH & Co. K G, assignee. Intracardial impedance measuring arrangement. United States patent application publication US 2005/0049646 A1. 2005 Mar. 3, now U.S. Pat. No. 7,844,335.
b) Chow T, inventor; Medtronic, Inc., assignee. Assessment of cardiac wall motion using impedance measurements. United States patent application publication US 2011/0054556 A1. 2011 Mar. 3.
c) Bornzin et al. inventors; Pacesetter, Inc., assignee. Method and system for hemodynamic optimization using plethysmography. United States patent application publication US 2011/0144711 A1. 2011 Jun. 16.

d) Kaye et al. Can transventicular intracardiac impedence measurement discriminate haemodynamically unstable ventricular arrhythmias in humans? Europace 2007, 9, 122-126.

e) Khoury D et al. Continuous right ventricular volume assessment by catheter measurement of impedance for anti-tachycardia system control. Pacing Clin Electrophysiology 1989, 12, 1918-1926.

Admittance Technologies has patented and published the following work leading up to this patent application, all of which is incorporated by reference. These include:

a) Feldman M D, Wu C, Mahler C, inventors; Admittance Technologies, Inc., assignee. Conductance catheter measurements and dual-frequency. U.S. Pat. No. 6,112,115. 2000 Aug. 29.

b) Feldman M D, Valvano J W, Pearce J A, inventors; Admittance Technologies, Inc., assignee. Multi-frequency conductance catheter-based system and method to determine LV function in a patient. U.S. Pat. No. 6,494,832. 2002 Dec. 17.

c) Feldman M D, Valvano J W, Pearce J A, Wei C, inventors; Admittance Technologies, Inc., assignee. Method and apparatus for determining cardiac performance in a patient with a conductance catheter. U.S. Pat. No. 7,925, 335. 2011 Apr. 12.

d) Feldman M D, Valvano J W, Pearce J A, inventors; Admittance Technologies, Inc., assignee. Method and apparatus for determining cardiac performance in a patient. United States patent application publication US 2009/0210020 A1. 2009 Aug. 20.

e) Feldman M D, Porterfield J E, Raghavan K, Valvano J W, Pearce J A, inventors; Board of Regents, The University of Texas Sys, assignee. Method and apparatus for monitoring an organ of a patient. United States patent application publication US 2010/0280397 A1. 2010 Nov. 4, now U.S. Pat. No. 8,706,219.

f) Porterfield et al. Left ventricular epicardial admittance measurement for detection of acute LV dilation. J Appl Physiol (2011) vol. 110 (3) pp. 799-806.

BRIEF SUMMARY OF THE INVENTION

The present invention pertains to an apparatus for treating a patient's heart. The apparatus comprises a sensor for measuring hemodynamics of the heart. The apparatus comprises a processing unit which receives the hemodynamics from the sensor and uses the hemodynamics to determine whether to shock the heart.

The present invention pertains to a method for treating a patient's heart. The method comprises the steps of measuring hemodynamics of the heart with a sensor. There is the step of receiving the hemodynamics from the sensor at a processing unit which uses the hemodynamics to determine whether to shock the heart.

BRIEF DESCRIPTION OF THE SEVERAL VIEWS OF THE DRAWING

In the accompanying drawings, the preferred embodiment of the invention and preferred methods of practicing the invention are illustrated in which.

DETAILED DESCRIPTION OF THE INVENTION

Figure 1:
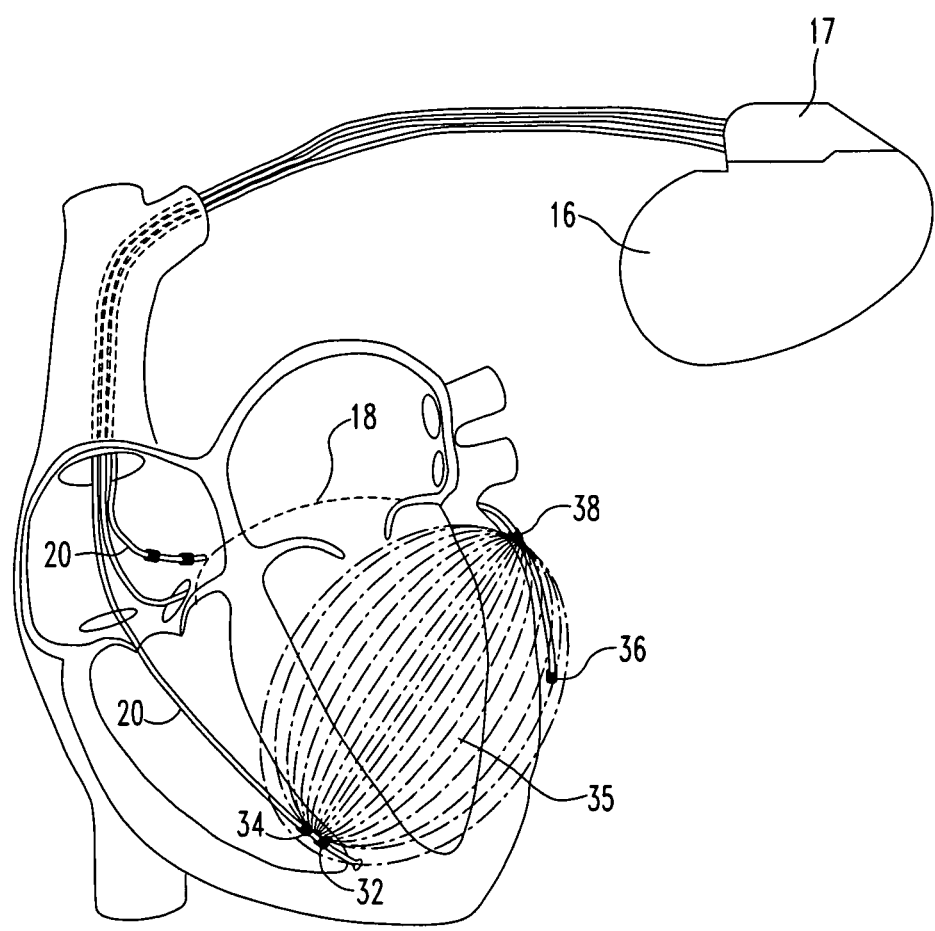
FIG. 1 shows four electrodes placed in or around the heart using two or more catheters in configurations for RV-LV and RA-LV. Electrodes 34 and 32 reside in the RV, 38 and 36 in the LV (coronary sinus). The other two electrodes are in the RA, and can be used instead of the RV electrodes.
Figure 2:
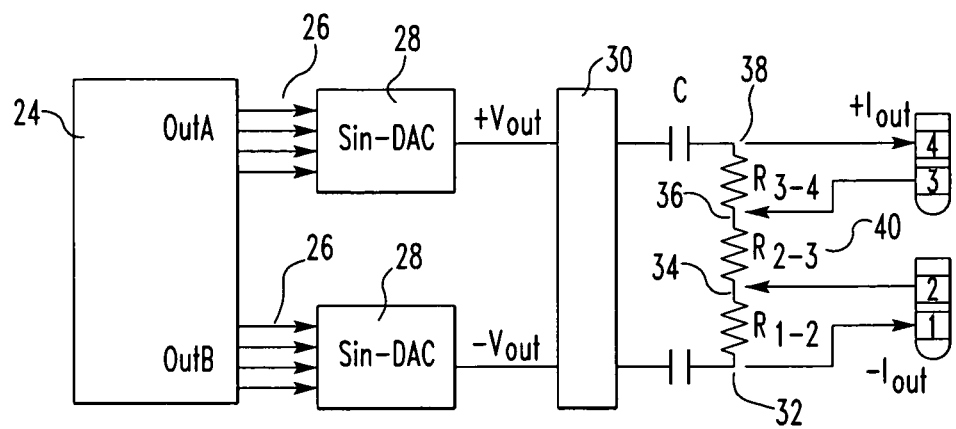
FIG. 2 is a block diagram of current stimulation of an example device. This example utilizes two RV electrodes from FIG. 1 and two LV electrodes from FIG. 1. This example also utilizes a new invention, previously disclosed, called a Sin-DAC that will create a 16-32 kHz sine wave current sources from digital microcontroller input.
Figure 3:
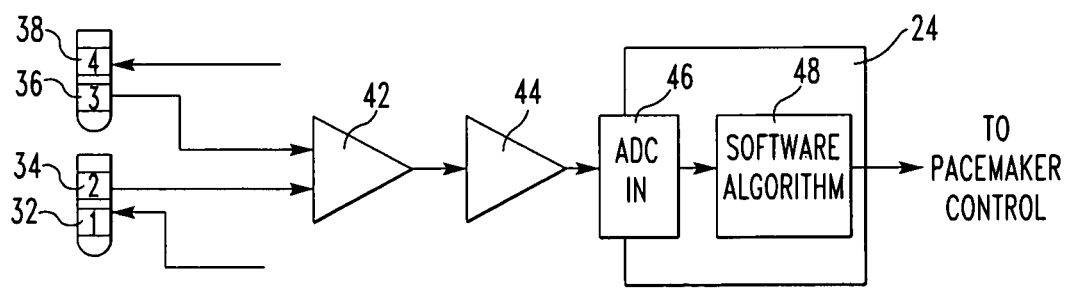
FIG. 3 is a block diagram of the voltage sensing circuitry of an example device.
Figure 9:
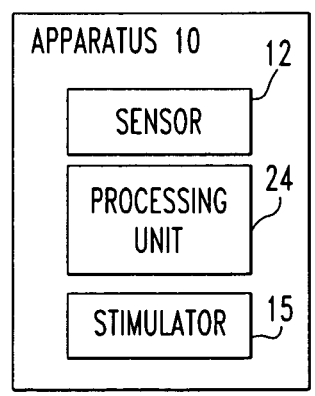
FIG. 9 is a block diagram of the apparatus of the present invention.

Referring now to the drawings wherein like reference numerals refer to similar or identical parts throughout the several views, and more specifically to FIGS. 1, 2 and 9 thereof, there is shown an apparatus 10 for treating a patient's heart. The apparatus 10 comprises a sensor 12 for measuring hemodynamics of the heart. The apparatus 10 comprises a processing unit 24, which receives the hemodynamics from the sensor 12 and uses the hemodynamics to determine whether to shock the heart.

The processing unit 24 may determine a real part and an imaginary part of impedance of the heart from the hemodynamics of the heart measured by the sensor 12. The processing unit 24 may determine the heart's myocardium and blood component. The processing unit 24 may determine volume in regard to the heart from the blood component to identify current stroke volume of the heart. The processing unit 24 may compare the current stroke volume to a baseline stroke volume, and if the current stroke volume is below the average stroke volume by at least a predetermined amount, the processing unit 24 produces a shock signal to shock the heart. The processing unit 24 may cause no action when the current stroke volume is approximately 80% to 100% of baseline stroke volume; wherein the processing unit 24 may increase sensing frequency of the stroke volume when the current stroke volume is approximately between 60% to 80% of baseline stroke volume; wherein the processing unit 24 may review the patient's ECG and sends a shock signal to shock the heart when the current stroke volume is between about 40% to 60% of baseline stroke file; and the processing unit 24 may send a shock signal to shock the heart when the current stroke volume is between approximately 0% to 40% of baseline stroke volume.

The apparatus 10 may include a stimulator 15 in electric communication with the processing unit 24 and the heart which is caused to shock the heart by the processing unit 24 when the processing unit 24 determines the hemodynamics are below a threshold.

The present invention pertains to a method for treating a patient's heart. The method comprises the steps of measuring hemodynamics of the heart with a sensor 12. There is the step of receiving the hemodynamics from the sensor 12 at a processing unit 24, which uses the hemodynamics to determine whether to shock the heart.

There may be the step of the processing unit 24 determining a real part and an imaginary part of impedance of the heart from the hemodynamics of the heart measured by the sensor 12. There may be the step of the processing unit 24 determining the heart's myocardium 56 and blood component 58. There may be the step of the processing unit 24 determining volume in regard to the heart from the blood component 58 to identify current stroke volume 62 of the heart. There may be the step of the processing unit 24 comparing the current stroke volume to a baseline stroke volume 64, and if the current stroke volume is below the average stroke volume by at least a predetermined amount, the processing unit 24 produces a shock signal to shock the heart. There may be the steps of the processing unit 24 causing no action when the current stroke volume is approximately 80% to 100% of baseline stroke volume; wherein the processing unit 24 increasing sensing frequency of the stroke volume when the current stroke volume is approximately between 60% to 80% of baseline stroke volume; wherein the processing unit 24 reviewing the patient's ECG and sending a shock signal to shock the heart when the current stroke volume is between about 40% to 60% of baseline stroke file; and the processing unit 24 sending a shock signal to shock the heart when the current stroke volume is between approximately 0% to 40% of baseline stroke volume. There may be the step of the processing unit 24 causing a stimulator 15 in electric communication with the processing unit 24 and the heart to shock the heart when the processing unit 24 determines the hemodynamics are below a threshold.

The present invention utilizes an algorithm to measure electrical impedance and electrical admittance across the heart that can determine if a patient that has an implantable cardioverter defibrillator (ICD) is in need of a therapy (a shock to restore sinus rhythm). Electrical impedance (Z) is the ratio of the effort divided by flow as electrical energy flows through an object. Electrical admittance (Y) is the ratio of flow divided by effort. The impedance and admittance of living tissue are complex numbers; this means electrical energy is both reduced in amplitude and delayed in time (phase shift) by the tissue during transfer. These electrical measurements can be used to determine heart volume, change in heart volume, and/or stroke volume.

The measurement of stroke volume is particularly interesting for its application to ICD technology. ICDs are often coupled with pacemakers designed for Cardiac Resynchronization Therapy (CRT) (1) and have multiple leads throughout the heart. An ICD determines if a patient is entering a dangerous arrhythmic event as a result of their heart disease, and saves their life by delivering a shock directly to the myocardium to return the heart to normal operation.

Currently, the algorithms that determine when to shock the heart are frequently wrong, and over a third of patients who receive an ICD receive an inappropriate shock within the first 1-3 years (2). This increases morbidity (3) and often leads to depression, and is associated with increased mortality (4) in patients. Inappropriate shocks occur because the electrical measurement used to determine if a shock is necessary (the ECG) is often misclassified or erroneously triggered. The present invention utilizes a new algorithm based on our electrical impedance/admittance device to determine when to shock based on hemodynamics, for the first time. Thus, the present invention links hemodynamics with abnormal cardiac rhythms for the first time.

Hemodynamics is defined as: "of or relating to the flow of blood within the organs and tissues of the body" by the New Oxford American Dictionary. In the present invention it relates specifically to the amount of blood pumped by the heart over a unit of time. Specifically, the term is used here to refer to the fact that the following can be measured: 1) the volume of blood within the heart chamber and 2) time, allowing one to derive the following: stroke volume, end-diastolic volume, end-systolic volume, contractility, motion of the epicardium, and rate of change of volume.

Given this information, a pacemaker/ICD can accurately determine when cardiac function is adequate (baseline stroke volume) or reduced due to an ongoing arrhythmia (reduced stroke volume from baseline) as part of the routine function of these devices. The benefits of our hemodynamic monitoring technology will be threefold. 1) battery life will be conserved with each inappropriate shock prevented, reducing the need for post-implant surgery to replace the battery, 2) unnecessary trauma (a possible reason for increased mortality) to the patient's heart will be prevented, (5), and 3) patients' quality of life will improve because of the decreased morbidity associated with reducing unnecessary shocks.

Operation (How the Invention Works):

The prior art describes the four-electrode technique. The four electrodes 32, 34, 36, 38 are either placed around the heart or in the heart as shown in FIG. 1. A sinusoidal current is applied to electrodes (1), 34 and (4), 38, and the resulting voltage is measured between electrodes (2), 32 and (3), 36. Although the description refers to a four-electrode configuration, the technique will also operate with any configuration using 2 or more electrodes. If the number of electrodes is less than four, then either or both electrode pairs 1-2 or 3-4 are shared. When using more than 4 electrodes, two electrodes are used to supply the sinusoidal current, and the remaining electrodes are used in pairs to measure the volume between the electrode pairs. The techniques that convert electrical measurements into heart volumes are also covered in prior art. The technique to remove the muscle component from admittance signals is explained in the prior art. This invention focuses on the technique used to determine hemodynamically unstable arrhythmias for the purpose of determining whether to deliver ICD therapy, and what type of therapy (eg. anti-tachycardial pacing versus cardioversion).

The invention will preferably reside entirely within the pacemaker can 16, and interface to the pacemaker leads 18, 20 through a connector 17. A can 16 utilizes many parts that are already present in current pacemakers such as a microcontroller 24 with an ADC 46, capacitors, resistors, operational amplifiers 42, and filters 44. Upon integration with the pacemaker, there will be large overlap in shared parts, causing a minimal size increase when the invention is added to a pacemaker. A can 16 is considered an enclosure.

Essentially any hermetically sealed, biocompatible container can be used as a can. Cans 16 are typically custom made, per each pacemaker company, so examples include the enclosures used by Medtronic of St. Jude Medical.

The invention makes a measurement of complex impedance by producing a sinusoidal current 35 between two electrodes (for example, the Coronary Ring 38, and the RV Ring 34), and sensing the voltage produced by this current from two or more other leads (for example, Coronary Tip 36, and RV Tip 32). Blood is less conductive than muscle, and has no measurable susceptance at low enough frequency (in the example, 20 kHz), and it is biological property that allows one to determine how much blood, and how much myocardium is in the current field. These concepts are discussed in prior art.

Because complex impedance is dependent on the relative amounts of myocardium and blood present within the current field 35, blood volume can be calculated in real time using this measurement of impedance using the results of our previous patents (d) and (e) above.

Figure 4:
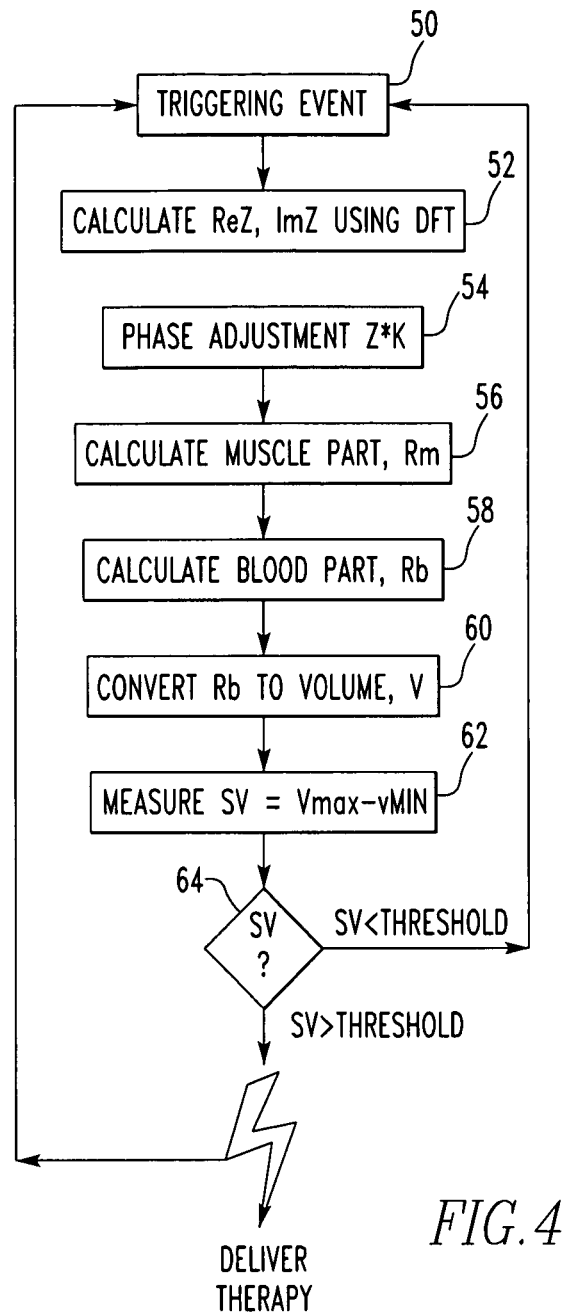
FIG. 4 shows an example algorithm for operation of the invention. This algorithm may be used with any triggering event, including hemodynamic events, electrical (ECG) events, or other signaling from the pacemaker/microcontroller such as regular time interval events, or pacing sequences.
Figure 5:
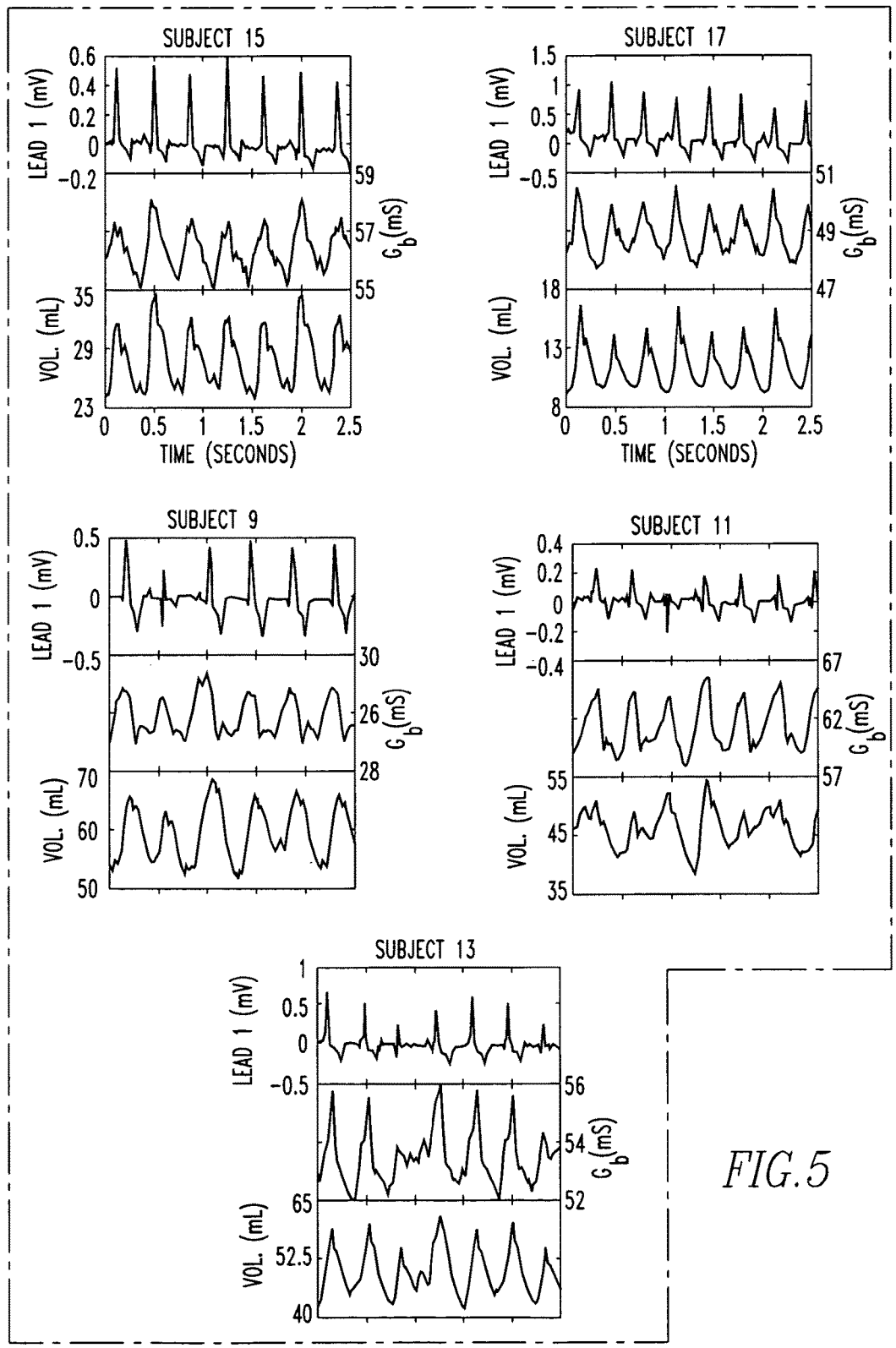
FIG. 5 shows lead 1 ECG, volume calculated from 2D sonomicrometry, and the conductance of blood measured using leads in the LV-RV configuration, in canines. Notice that the conductance of blood tracks sonomicrometry volume on a beat-to-beat basis.

When coupled with an ICD/Bi-ventricular pacemaker, the device uses the algorithm outlined in FIG. 4 to determine if VT is occurring and a shock is necessary. This algorithm may be used with any triggering event, including hemodynamic events, electrical (ECG) events, or other signaling from the pacemaker/microcontroller such as regular time interval events, or pacing sequences. The threshold determination should be set on a per-patient basis, and could either be at the prescribing physician's discretion, or a default value set by the manufacture. Detection of SV will occur on a beat-to-beat basis, and will use a running average to determine the relative change in SV over time. Therapy (a shock) is delivered at a time when the stroke volume is sufficiently low to require an intervention by the device, somewhere between 0-60% of the baseline for a 10-30 beat period. This percentage of the baseline is known as the 'threshold', and is the determining factor for when the patient is shocked. The number of heart beats used to determine the running average of SV will be heart rate dependent, requiring more beats of certainty when the heart is beating faster, and fewer when the heart is beating slower. In this way, the SV signal will be 'weighted' to prevent short arrhythmias from triggering a shock.

Baseline will be determined upon programming, and at each hospital visit by the patient's physician. This baseline can be an average of multiple beats (perhaps 10) at a normal, seated position upon implant. Each time the patient is shocked with existing devices, a hospital visit is currently required, and this visit will serve as the adjustment point for the threshold. Here again, the physician will be the one to adjust the threshold.

An adaptively changing threshold can be adopted for more slowly changing SV, where shocking is not necessary but patient condition is changing. For example, as a running average is taken over a larger and larger number of heartbeats, the running average represents a much slower 'drift' that might require an adjustment of the baseline threshold without making it necessary to deliver therapy. The number of beats that determines the 'drift' determination will be chosen by the physician based on how stable the patient's condition is. A more stable (unchanging) patient condition requires a longer running average, while a more variable (changing) patient condition requires a shorter running average.

Instead of a threshold, using a "confidence interval" will be closest to what is planned upon implementation. This is subtly different than a threshold because if, for example, the patient's SV drops to zero, there is an immediate need to shock. However, if the patient's SV drops to 60%, it is less clear whether this is a life-threatening situation. In this case, it may be better to establish a better measurement before making the determination to shock. An example of this would be:

Confidence Intervals:

CI1: current SV at 80%-100% of baseline SV|Action: None|Sensing: no change

CI2: current SV at 60-80% of baseline SV|Action: None|Sensing: Increase frequency of sensing SV to more precisely determine an event in need of therapy CI3: current SV at 40-60% of baseline SV|Action: Check other metrics to improve confidence that a shock is necessary|Sensing: Check other metrics that might indicate therapy is necessary including but not limited to ECG to determine if electrical activity corroborates the drop in SV through rate, rhythm, and morphology discrimination CI4: current SV at 0-40% of baseline SV|Action: Shock|Sensing: none, this marks a dangerous condition in need of therapy, and no other sensing is necessary."

Figure 10:
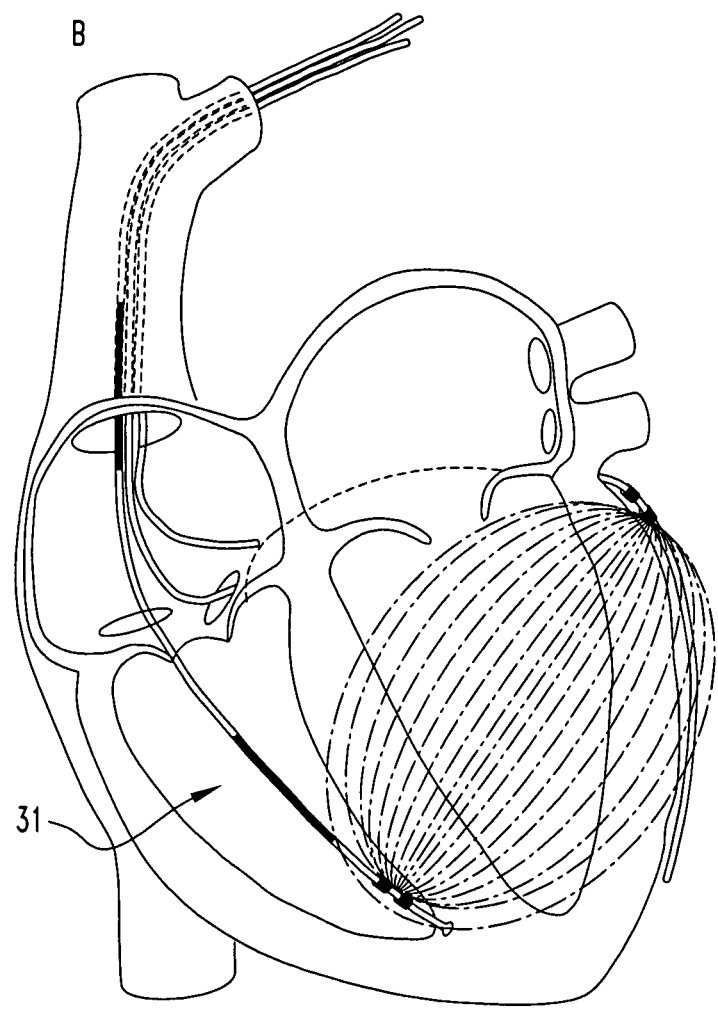
FIG. 10 shows a shocking electrode and the heart.

First, a triggering event 50 is necessary, which can be a timed event that happens at a regular interval, or one of the many other algorithms for determining that a shock may be necessary. Only running the invention when deemed necessary by a lower power device would allow for maximum energy conservation. Once it is determined that a hemodynamic measurement is necessary, the device will measure the Real and Imaginary parts of Impedance 52, taking advantage of the DFT to conserve power. After a phase calibration 54, the myocardium 56 and blood components 58 will be calculated. Optionally, the blood component will be converted to volume at this point 60. The amount of resistance between the two electrodes can serve as a surrogate for blood volume if desired, to save time and power in the device. At this point, the Stroke Volume (SV) is known 62 through the difference of the maximum and minimum blood volume (or resistance, if desired). During an event, the SV will be compared 64 to average values of SV to determine if it is sufficiently low to require a shock (therapy). In the event that the SV drops to a value appreciably below the baseline SV, it will become necessary to shock the patient to prevent sudden death. This therapy will optimally be delivered using a shocking electrode 31, as shown in FIG. 10, but optionally could be delivered using any combination of electrodes 32, 34, 36, 38, or those on the RA lead 20. If the SV detected is consistent with those recorded previously, the patient may be experiencing a stable tachycardia, and no therapy is necessary. If this is the case, the entire procedure will be repeated to determine if the arrhythmia still exists, or if it was self-terminating.

State of the art in VT detection involves electrocardiographic (not hemodynamic) measurement, because most pacemakers/ICDs are already outfitted with the equipment necessary to measure ECG. This makes electrical measurement the most obvious solution for arrhythmia classification. However, these algorithms have a low specificity, due to mistakes in classification of ECGs. For this reason, a more direct measurement of hemodynamics would be a significant advance to the ICD industry, because it incorporates how physicians are trained to treat these patients.

EXAMPLES

Dopamine Study

In large animals, iv dopamine was given to increase stroke volume at 1.25, 2.5, 5, 7.5, and 10 µg/kg/min for 10 minutes at each dose. In the same preparation, the ascending aorta was instrumented for flow to determine real time stroke volume (SV) as a gold standard. Additionally, pacemaker leads were placed in the standard position for a bi-ventricular pacemaker (RA, RV, and Coronary Sinus on the LV freewall). The hypothesis determined was that as the dose of dopamine increased, the stroke volume would be detected by both the present invention, and the gold standard.

Pacing Study

In the same large animals, the heart was constantly-paced increasingly faster using a DOO configuration (both RA and RV leads were paced, with AVd set to 30 ms less than intrinsic AVd, measured during atrial pacing). The point of this study was also to reduce the stroke volume measured by both flow and the pacemaker leads through the reduction of preload due to tachy-pacing.

VT Studies

In the same large animals, the right ventricle only was constant-rate paced (VOO configuration) using rates faster than the intrinsic heart rate. This causes a stable Ventricular Tachycardia that shows our measurements' utility at detecting irregular heartbeats and stroke volumes. In this study, volume was measured using 2D sonomicrometry and used as the gold standard, while volume measurements were also taken using the invention.

IVC Occlusion Studies

In the same large animals, a transient Inferior Vena Cava (IVC) occlusion was performed to determine whether the invention could correctly predict dynamic volume and SV due to reduced preload. IVC occlusions are less clinically applicable than the pacing study (above) and only convey how quickly the invention can respond to a decreasing volume.

Results

Figure 6A:
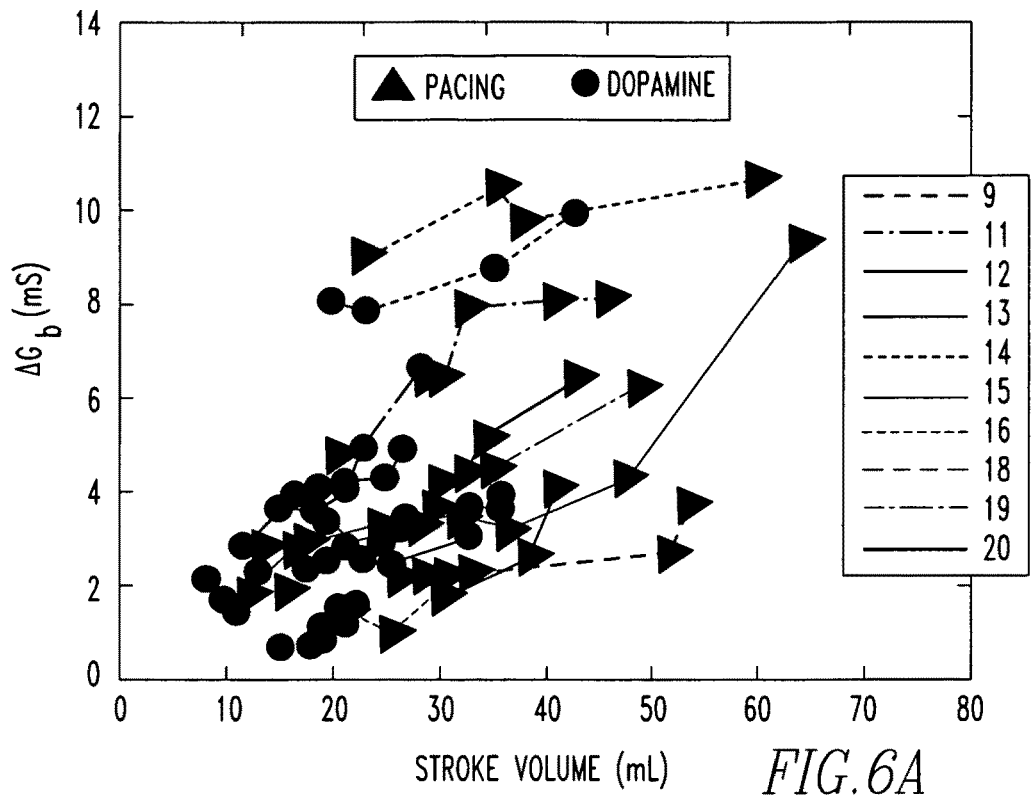
FIGS. 6A-6D show results of a dopamine/pacing experiment.
Figure 6B:
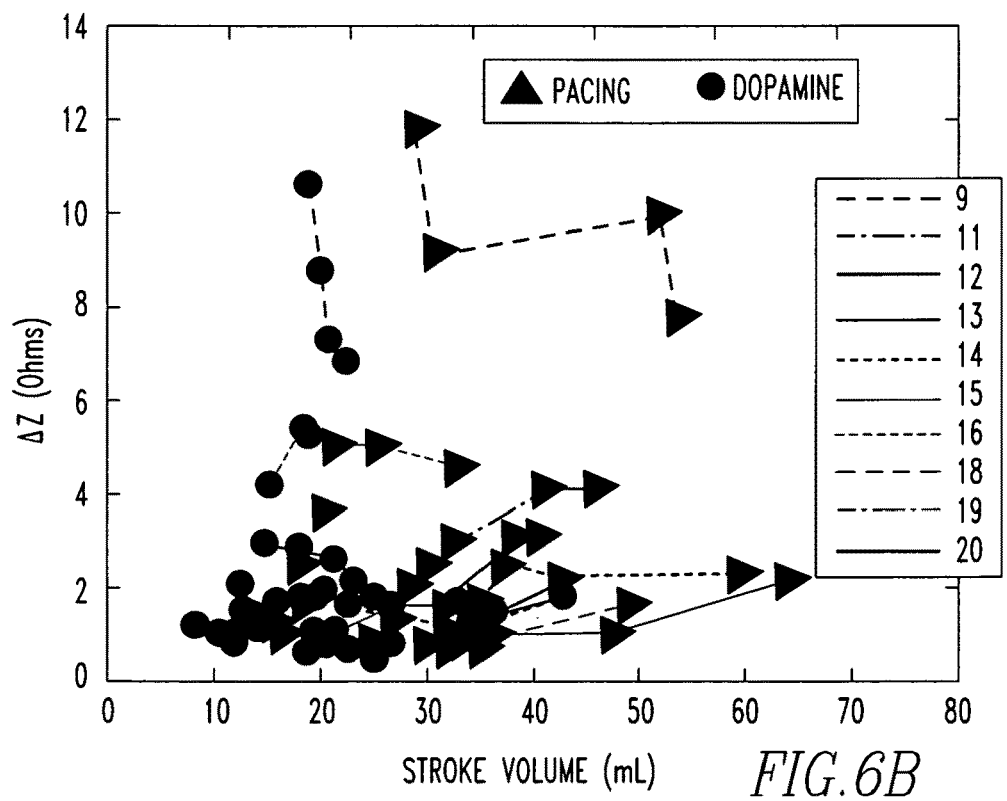
Figure 6C:
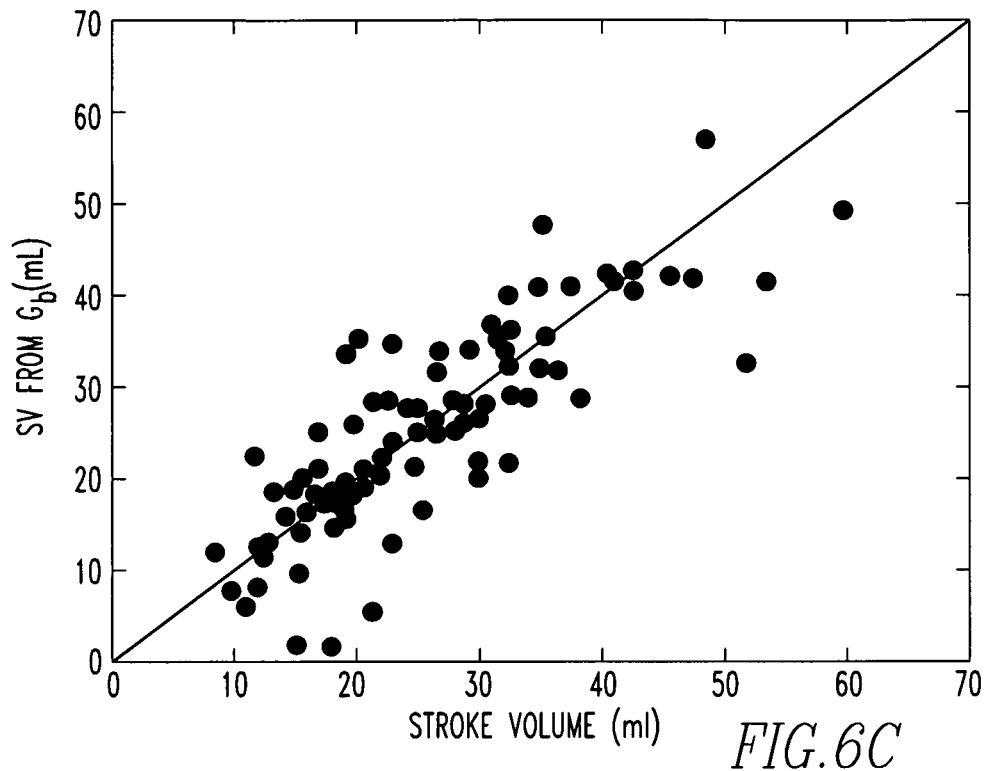
Figure 6D:
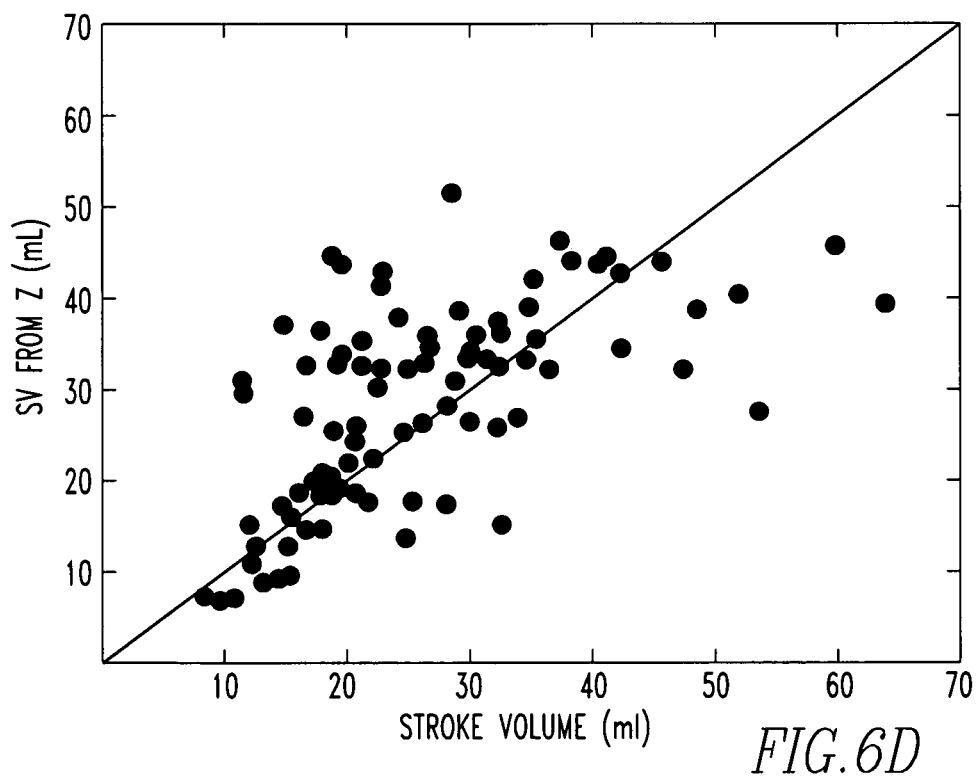
Figure 7:
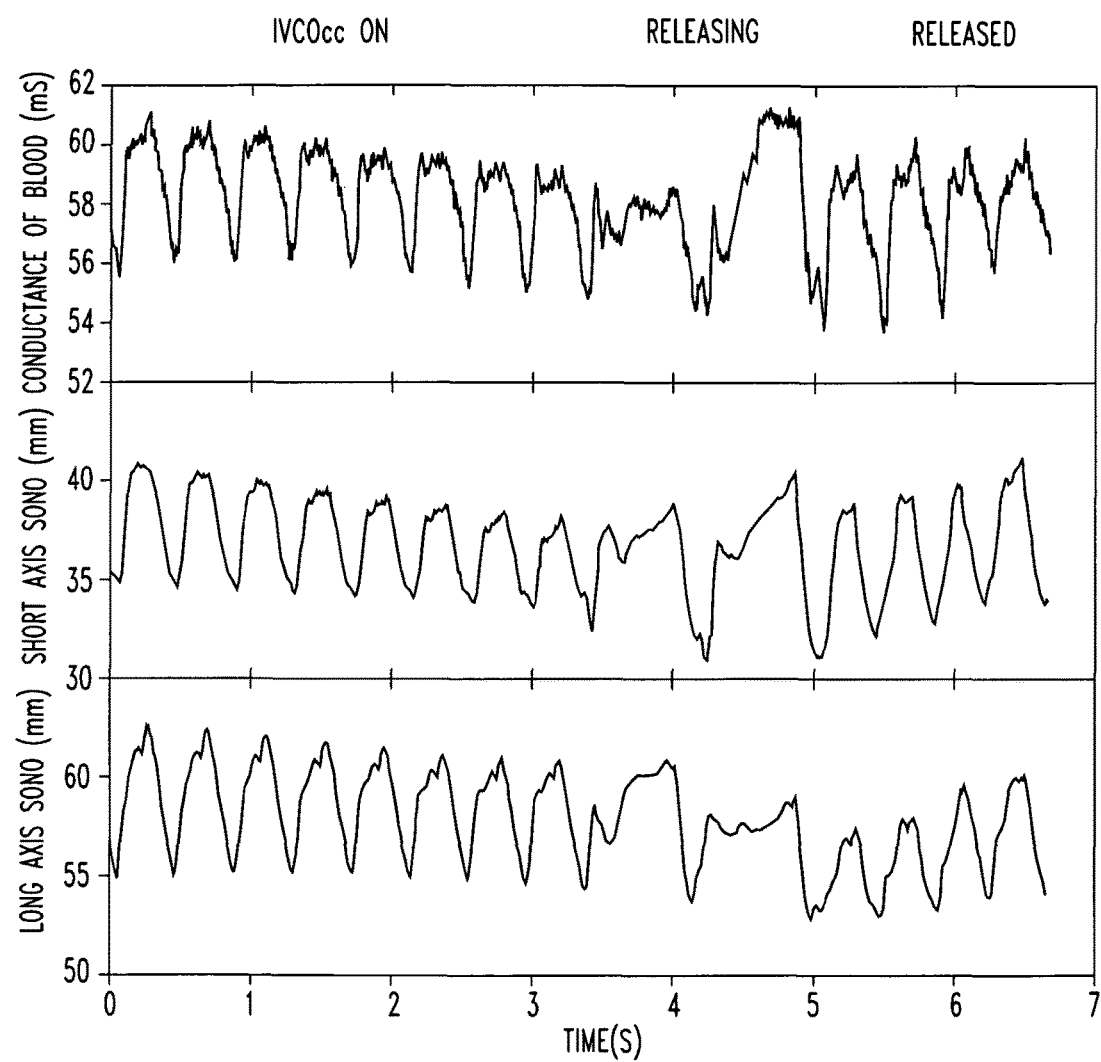
FIG. 7 shows the results of an IVC occlusion when taking a measurement configured as in FIG. 1. As can be seen in the figure, the conductance of blood measured from epicardial leads 18, 20, closely track actual distances measured via sonomicrometry.
Figure 8:
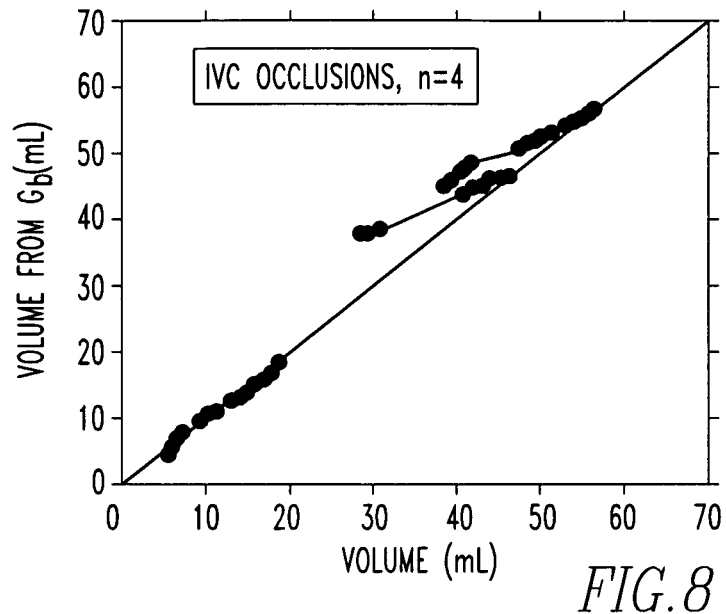
FIG. 8 is a graph showing after converting the measurement to volume, as in FIG. 6B, IVC occlusion data also tracks volume from sonomicrometry.

The results are shown in FIGS. 6A-6D and 7. The Dopamine and Pacing study results for the configuration shown in FIG. 1 are shown in FIG. 6A. As the standard for volume (2D sonomicrometry) increases in stroke volume (SV), the invention shows an increase in stroke conductance (AGb, circles). Likewise, a decrease in pacing rate corresponds with an increase in SV. (AGb, triangles). When the same data are analyzed using magnitude only, it is similar to FIG. 6B. These studies show that the use of complex admittance is necessary to allow the tracking of volume.

The x-axis on all of these panels is SV measured using 2D sonomicrometry. As this value increases, the measured value from our invention should increase. Panel 6A: The results of LV-RV configuration during the dopamine and pacing experiments. Panel 6B: The same results as in Panel 6A, but without the muscle signal separated. This is one of the main advantages of our admittance technique, because other devices do not have the capability of performing the calculation necessary to remove the muscle. It is obvious from this figure that panel 6A shows correlation between Gb and SV, and panel B does not show correlation between Z and SV. Panel 6B and 6D show the same results as FIGS. 6A and 6C, but with a simple correction factor to convert to volume. More complicated equations could be used for better correlation, but this simple multiplicative correction shows that SV can be accurately estimated using the invention. Notice the larger "spread" in panel 6D.

Currently, Dual Chamber ICDs are the state-of-the-art in determining when a shock is appropriate or inappropriate. These devices are focused on determining the stability (or instability) of a tachycardic event using intracardiac ECG through rate discrimination, rhythm discrimination, and morphology discrimination of ECG signals. It is believed the current invention will be the first (and only) device that can determine a measure of hemodynamic stability (stroke volume), that incorporates how physicians are trained to think regarding when to administer cardioversion, or apply more conservative therapy.

DRAWINGS—REFERENCE NUMERALS

10—Apparatus
12—Sensor
15—Stimulator
16—Pacemaker enclosure, where the invention will interface with the electrodes.
17—Connector for the pacemaker leads, which will interface with the invention enclosed in 16, and connect to the LV 18, RA and RV 20 leads.
18—A lead consisting of two electrodes placed on the LV epicardium (in the coronary sinus) using an LV lead.
20—The RV and RA leads each consisting of two electrodes placed in the heart (in a ventricle or atrium).
24—Microcontroller or digital logic: One example of an existing microcontroller that can be used is the Texas Instruments MSP430F2013. This microcontroller has 2048 bytes of Flash EEPROM, 128 bytes of RAM, and runs at 16 MHz. It can be used to measure volume, and comes in a 16-pin surface mount package occupying 4 by 4 by 1 mm.
26—Digital outputs from microcontroller.
28—Object of our previous patent, allows the use of digital logic to drive a sinusoidal current through the electrodes.
30—OPA330AIDCKT op amp used to convert the Sin-DAC output to sinusoidal current at 20 kHz.
31—Shocking electrode
34, 38—Stimulation (current) electrodes
35—The path of current as it flows between the current electrodes.
32, 36—Voltage (return) electrodes.
42—Low power amplifier: One example of a low power amplifier is the Texas Instruments INA322. This instrumentation amp runs with 490 microA of supply current, and has bandwidth of 2 MHz at a gain of 25.
44—Low Pass Filter (optional). The tradeoff for not using this filter is lower power for lower signal to noise ratio.
46—Input voltage is sampled using the microcontroller ADC.
48—The data are run through a software algorithm that converts the measurement to a meaningful control signal for the pacemaker control.
50—The triggering event is a physiological event that determines that a hemodynamic event is necessary. One possible event could be a rate discriminated tachycardia. The algorithm can run in addition to any other VT detection algorithm to increase specificity.
52—Calculation of the Real and Imaginary parts of impedance is described in the prior art.
54—Calibration of the Imaginary part.
56—Calculation of the muscle component of impedance is necessary for accurate calculation of the blood component, and is described in the prior art.
58—Calculation of the blood component of impedance.
60—Converting from blood impedance to volume is optional, as the peak to peak value of Rb can be used as the control signal.
62—Stroke volume calculation.
64—SV Threshold will be a percentage of normal SV. Symptomatic VT occurs because of lowered cardiac output.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

The invention claimed is:

1. An apparatus for treating a patient's heart comprising: a pacemaker can; a sensor for measuring hemodynamics of the heart, the sensor including pacemaker leads, the sensor uses a sinusoidal current between 2 electrodes of the pacemaker leads and senses a voltage produced from the sinusoidal current; a processing unit disposed in the can which receives the hemodynamics from the sensor and uses the hemodynamics to determine whether to shock the heart, pace the heart, or observe the heart and offer no therapy, the processing unit determines a real part and an imaginary part of impedance of the heart from the hemodynamics of the heart measured by the sensor, the processing unit determines the heart's myocardium and blood component, the processing unit determines volume in regard to the heart from the blood component with the myocardium component removed to identify current stroke volume of the heart, the processing unit compares the current stroke volume to a baseline stroke volume, and if the current stroke volume is below an average stroke volume by at least a predetermined amount, the processing unit produces a shock signal to shock the heart; and a stimulator in electric communication with the processing unit and the heart which is caused to shock the heart by the processing unit when the processing unit determines the hemodynamics are below a threshold, the stimulator and the sensor and the processing unit together using an average current of less than 23 mA in operation over time, wherein the processing units causes no action when the current stroke volume is approximately 80% to 100% of baseline stroke volume; wherein the processing unit increases sensing frequency of the stroke volume when the current stroke volume is approximately between 60% to 80% of baseline stroke volume; wherein the processing unit reviews the patient's ECG and sends a shock signal to shock the heart when the current stroke volume is between about 40% to 60% of baseline stroke file; and the processing unit sends a shock signal to shock the heart when the current stroke volume is between approximately 0% to 40% of baseline stroke volume.

2. A method for treating a patient's heart comprising the steps of: measuring hemodynamics of the heart with a sensor, the sensor including pacemaker leads, the sensor uses a sinusoidal current between 2 electrodes of the pacemaker leads and senses a voltage produced from the sinusoidal current; receiving the hemodynamics from the sensor at a processing unit disposed in a pacemaker can which uses the hemodynamics to determine whether to shock the heart, pace the heart, or observe the heart and offer no therapy, the processing unit determining a real part and an imaginary part of impedance of the heart from the hemodynamics of the heart measured by the sensor, the processing unit determining the heart's myocardium and blood component, the processing unit determining volume in regard to the heart from the blood component with the myocardium component removed to identify current stroke volume of the heart, the processing unit comparing the current stroke volume to a baseline stroke volume, and if the current stroke volume is below an average stroke volume by at least a predetermined amount, the processing unit produces a shock signal to shock the heart; and the processing unit causing a stimulator in electric communication with the processing unit and the heart to shock the heart when the processing unit determines the hemodynamics are below a threshold, the stimulator and the sensor and the processing unit together using an average current of less than 23 mA in operation over time, including the steps of the processing unit causing no action when the current stroke volume is approximately 80% to 100% of baseline stroke volume; wherein the processing unit increasing sensing frequency of the stroke volume when the current stroke volume is approximately between 60% to 80% of baseline stroke volume; wherein the processing unit reviewing the patient's ECG and sending a shock signal to shock the heart when the current stroke volume is between about 40% to 60% of baseline stroke file; and the processing unit sending a shock signal to shock the heart when the current stroke volume is between approximately 0% to 40% of baseline stroke volume.

3. The apparatus of claim 2 including a housing that is adapted to be implanted in the patient, the processing unit disposed in the housing.

4. The apparatus of claim 1 wherein the processing unit causes the sinusoidal current to be produced.

5. The apparatus of claim 4 wherein the sinusoidal current is a sine wave between 16 and 32 kHz.

6. The apparatus of claim 5 including a Sin-DAC in communication with the processing unit which produces the sine wave.

7. The method of claim 2 including the step of the processing unit causing the sinusoidal current to be produced.

8. The method of claim 7 wherein the sinusoidal current is a sine wave between 16 and 32 kHz.

9. The method of claim 8 including a Sin-DAC in communication with the processing unit, and there is the step of the Sin-DAC producing the sine wave.

* * * * *